United States Patent [19]

Nadal et al.

[11] Patent Number: 5,800,515
[45] Date of Patent: Sep. 1, 1998

[54] PROSTHESIS IMPLANTABLE IN A HUMAN OR ANIMAL DUCT SUCH AS A STENT OR A PROSTHESIS FOR ANEURISM

[75] Inventors: Guy Nadal, Poitiers; Gérard Chevillon, Montrouge; Jean-Philippe Cottenceau, Antony, all of France

[73] Assignee: B. Braun Celsa (Societe Anonyme), Chasseneuil-Du-Poitou

[21] Appl. No.: 690,979

[22] Filed: Aug. 1, 1996

[30] Foreign Application Priority Data

Aug. 3, 1995 [FR] France ............... 95 09473

[51] Int. Cl.$^6$ ............................................. A61F 2/06
[52] U.S. Cl. ............................................. 623/1
[58] Field of Search ............... 623/1, 11, 12; 606/194, 195, 198

[56] References Cited

U.S. PATENT DOCUMENTS

| | | |
|---|---|---|
| 4,856,516 | 8/1989 | Hillstead . |
| 4,994,071 | 2/1991 | MacGregor . |
| 5,016,963 | 5/1991 | Pan . |
| 5,019,090 | 5/1991 | Pinchuk .................. 623/1 |
| 5,133,732 | 7/1992 | Wiktor .................... 623/1 |
| 5,135,536 | 8/1992 | Hillstead ................. 623/1 |
| 5,387,235 | 2/1995 | Chuter . |
| 5,609,627 | 3/1997 | Golcoechea et al. ....... 623/1 |
| 5,643,339 | 7/1997 | Kavteladze et al. ....... 623/1 |

FOREIGN PATENT DOCUMENTS

| | | |
|---|---|---|
| 0177330 | 4/1986 | European Pat. Off. . |
| 9521592 | 8/1989 | European Pat. Off. . |
| 0335341 | 10/1989 | European Pat. Off. . |
| 0421729 | 4/1991 | European Pat. Off. . |
| 0508473 | 10/1992 | European Pat. Off. . |
| 0565251 | 10/1993 | European Pat. Off. . |
| 0657147 | 6/1995 | European Pat. Off. . |
| 2678508 | 4/1991 | France .................. 623/1 |
| 9206734 | 4/1992 | WIPO . |
| 9641590 | 12/1996 | WIPO . |

*Primary Examiner*—Michael J. Milano
*Assistant Examiner*—Tram Anh T. Nguyen
*Attorney, Agent, or Firm*—Rothwell, Figg, Ernst & Kurz

[57] ABSTRACT

A prosthesis which can be implanted in a human or animal duct to ensure a passageway in the duct. The prosthesis is formed from several filaments which have corrugations and which are wound to define a tubular surface. The corrugations form an advantageously zig-zagged series of rings that are stepped along the length of the prosthesis, with corrugated portions of the individual filaments constituting portions of two or more separate ones of the rings.

13 Claims, 4 Drawing Sheets

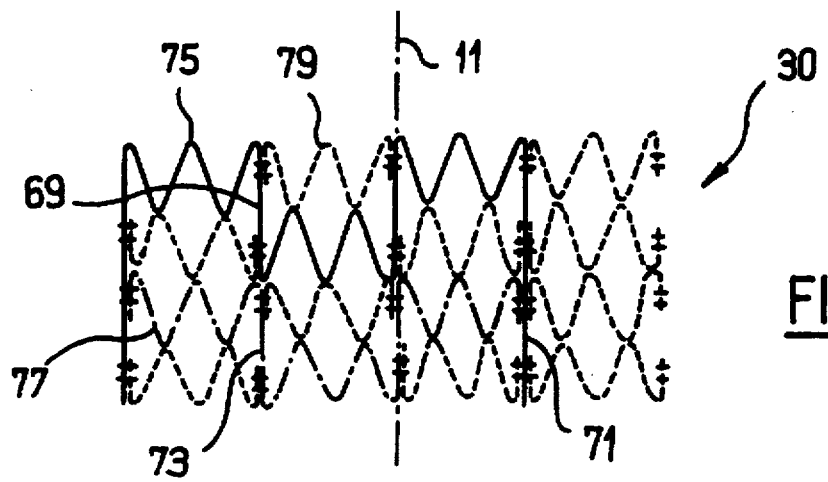
FIG_7
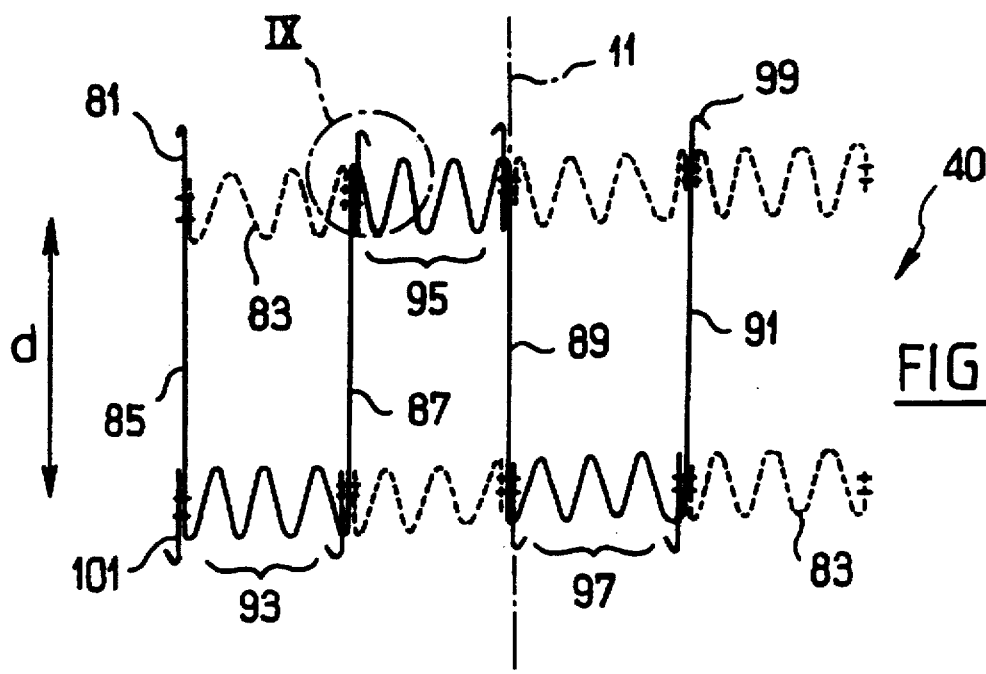
FIG_8
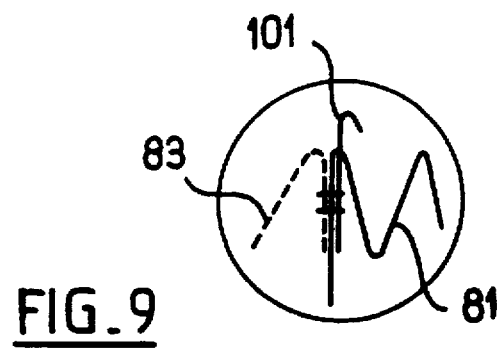
FIG_9

PROSTHESIS IMPLANTABLE IN A HUMAN OR ANIMAL DUCT SUCH AS A STENT OR A PROSTHESIS FOR ANEURISM

FIELD OF THE INVENTION

The invention relates to the field of tubular prostheses which can be implanted in an anatomical duct of a human or animal body to maintain, or possibly re-establish, a passageway in the duct.

Of prostheses of this type, the invention relates especially to vascular prostheses and, in particular, to wall dilatators or wall struts (also known as stents) or to prostheses for aneurism having not only with structural elements, like stents, but also external covering sleeves to channel the blood flow and, in general, also having means such as hooks carried by the above-mentioned structural elements for anchoring the prosthesis to vessel wall.

BACKGROUND OF THE INVENTION

Numerous examples of such stents and other prostheses for aneurism exist in the prior art. There may be mentioned, for example, U.S. Pat. No. 4,994,071; U.S. Pat. No. 4,856,516; EP 335 341; EP 177 330; EP 565 251; U.S. Pat. No. 5,387,235; and EP 508 473.

U.S. Pat. No. 4,856,516 discloses a prosthesis having a tubular surface with a tube axis and comprising a single filament (in this case, a metal filament a few tenths of a millimeter in diameter) having corrugations which are wound in order to define the tubular surface of the prostheses by portions.

However, existing prostheses (in particular, the prosthesis of U.S. Pat. No. 4,856,516) do not necessarily provide optimum reliability and balance between the necessary flexibility of the prosthesis (bearing in mind its implantation position) and rigidity (bearing in mind its function in the duct).

With respect to forked prostheses, U.S. Pat. No. 4,994,071 discloses a prosthesis which has a main tubular branch dividing into two secondary tubular branches and which comprises several filaments which have corrugations wound to define the tubular branches, respectively, by tube portions. That patent teaches the common manufacture of the main tubular branch and one of the secondary tubular branches, the connection of the other secondary branch being carried out only by means of a longitudinal strut filament which mirrors the longitudinal strut filament of the first two branches by being bent, like it, towards the exterior of the stent to ensure that the two secondary branches of the prosthesis are spaced apart from one another. The prosthesis of U.S. Pat. No. 4,994,071 generally has the same disadvantages as those of U.S. Pat. No. 4,856,516. Additionally, it will be noted that the corrugations of the filaments are rectangular. This can cause problems if it is desired to implant the prosthesis percutaneously using a tube or catheter having a very small diameter, i.e., on the order of 2 to 5 mm.

SUMMARY OF THE INVENTION

In view of these concerns, the invention provides a prosthesis which is especially reliable in use and which is easy to manufacture and to implant. The prosthesis can be used as a simple or a forked stent or as a structural element for a simple or a forked prosthesis for aneurism, or even in other applications, for example, in other anatomical ducts.

In order to achieve that object, the prosthesis of the invention is characterised especially in that it comprises several filaments, each filament defining only one portion of the tubular surface of the prosthesis.

If the prosthesis is forked, the filaments in question will advantageously define, for each of the branches of the prosthesis, only one portion of that branch.

The solution of the present invention applies to both "simple" and "forked" prostheses.

With the intention of promoting the reliability of the prosthesis and the conditions of manufacture and use, while ensuring the desired balance between both radial and axial flexibility and rigidity, another feature of the invention provides that the filaments of the prosthesis pass advantageously from one tube portion to another. It is therefore possible to produce several tube portions using the same thread, thus reducing the problems of joining the filaments to one another.

Thus, the invention provides a medical prosthesis implantable in a living body and comprising a frame having at least one tube axis and including several levels or "rings" of tubular portions which are substantially coaxial and which are formed individually by a corrugated or zig-zag structure having peaks or apices between which elongate segments extend, two tubular portions being connected to one another by at least one segment of the structure. Elongate segments of the structure, including those which connect two tubular portions to one another, are formed by at last one relatively rigid thread such as a metal thread a few tenths of a millimeter in diameter or a thread of suitable plastic material. At least one segment has a length greater than the segments forming the meanders have these longer segments pass from a first level or step of tubular portion to a second level. Connecting means such as spot welds connect the segments of greater length to first and second corrugated portions belonging, respectively, to the first and second levels of tubular portion. Thus, the longer sections provide for cohesion of the structure, which may be in particular a stent.

Even though, within the scope of the invention, the tube portions formed by the corrugations of the filaments of the prosthesis may be arranged in a coil to define the tubular surface or surfaces of the prosthesis, it is preferable that the tubular portions be stepped along the axis of the tube, and that each portion extending circumferentially be defined by a succession of corrugations of different filaments which are arranged in series and wound onto themselves to form a closed ring.

In this manner, when the prosthesis is implanted and has to exert an outwardly directed radial force to maintain the desired passageway in its implantation duct, the force will be distributed radially relative to the axis of the prosthesis. (This is not the case of prostheses formed by helical winding.)

Another feature of the invention provides that the filament corrugations are advantageously zig-zags having bent peaks connected by intermediate portions which extend transversely to the tube axis concerned. The peaks are angularly spaced from one another when the prosthesis is in a first, expanded configuration; two successive portions of each zig-zag are arranged close to one another and extend substantially parallel to one another and to the tube axis when the prosthesis is in a second, compacted configuration that is narrower than the first in order to enable it to be implanted.

In particular in the case of such zig-zag shapes, a complementary feature of the invention also provides that two adjacent filaments are arranged locally against one another over a certain length in order to be secured to one another over that length, especially by welding.

When the prosthesis of the invention—and especially a forked prosthesis—comprises a series of radial corrugated rings, the production of a fork can advantageously be carried out in steps and, starting from the step where the main branch divides into its two secondary branches, by closing onto themselves the corrugations of the filaments in two independent portions arranged side-by-side, without the annular corrugations so formed being connected to one another. This promotes the natural spacing between the two branches.

DESCRIPTION OF THE DRAWINGS

Embodiments of the invention will be described in more detail below with reference to the appended drawings, in which

FIGS. 6 and 7 show two alternative embodiments of a prosthesis, unrolled flat;

FIGS. 8, 9, and 10 demonstrate the construction of a tubular prosthesis for aneurism.

DETAILED DESCRIPTION OF THE INVENTION

Figure 1:
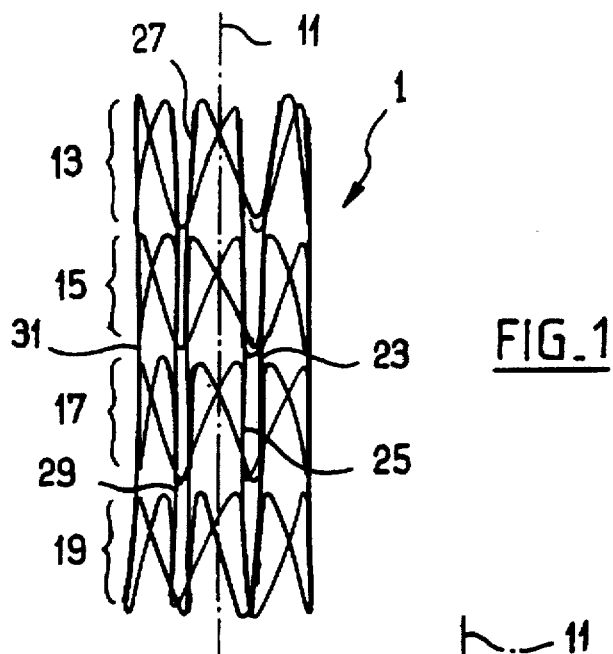
FIGS. 1 and 2 show a first embodiment of a simple tubular prosthesis of the stent type in a perspective view and as unrolled flat, respectively.

FIG. 1 shows a vessel dilatator 1, commonly known as a stent. The dilator 1 can also be used as the basic structure for a prosthesis for aneurism, or even for a prosthesis to be implanted in an anatomical duct other than a vessel such as, for example, the trachea or the esophagus. (The element 1 will be referred to hereinafter, in general, as a stent, bearing in mind the common use of this term.)

Figure 2:
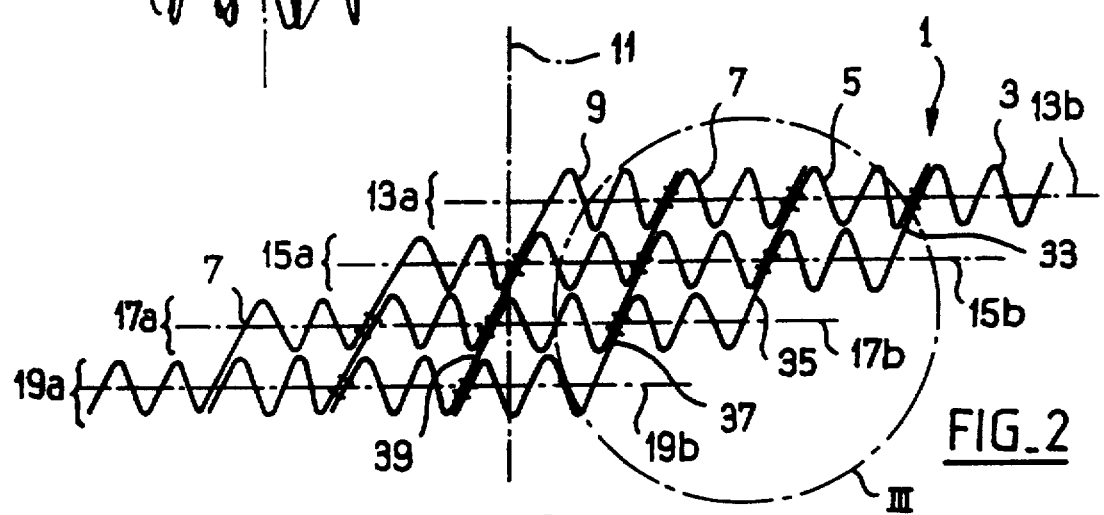

The stent 1 is basically formed from several filaments, e.g., as can be seen more clearly in FIG. 2 where the filaments have been marked 3, 5, 7, and 9. The filaments may in particular be metal filaments a few tenths of a millimeter in diameter, for example filaments produced from a steel-based alloy as commonly used for a number of vascular prostheses such as filters, stents, etc. It will be noted that each of the filaments 3, 5, 7, 9 has corrugations, such as those marked 5a, 5b, 5c, 5d in the case of the filament 5 in FIG. 3. Instead of giving these corrugations a crenellated or S-shaped form, it may be preferable to give them a zig-zag shape with, as shown most clearly in FIG. 3 in the case of one zone of the thread 7, peaks such as 7a which are bent at fairly acute angles and which are connected to one another in alternate directions by preferably rectilinear (i.e., straight) intermediate portions, such as 7b and 7c.

It will be appreciated that one of the advantages of this zig-zag configuration is that, for implantation, the prosthesis can be compacted radially with respect to its longitudinal axis 11 to a first, reduced diameter $d_1$, which may be on the order of from 1.5 to 2.5 mm. In this configuration, it can be introduced into a fine introducing tube permitting percutaneous implantation, e.g., by the known SELDINGER method. The zig-zag shape also allows for a second diameter, $d_2$, which is widened relative to the first, when the prosthesis has reached its place of implantation and can be spread radially in the chosen duct.

If the filaments 3, 5, 7, 9 are made from spring-type metal, the prosthesis 1 may be of the radially "self-expanding" type. In other words, it will occupy its reduced diameter $d_1$ while constrained, and when this radial constraint is removed, the prosthesis will automatically expand radially until it reaches the configuration shown in FIG. 1. In that configuration, the intermediate portions of the filaments are spaced angularly from one another relative to the axis 11 whereas, when the prosthesis has its reduced diameter configuration, the filaments are substantially placed against one another, substantially parallel to this axis 11, such as is known in the art.

Figure 3:
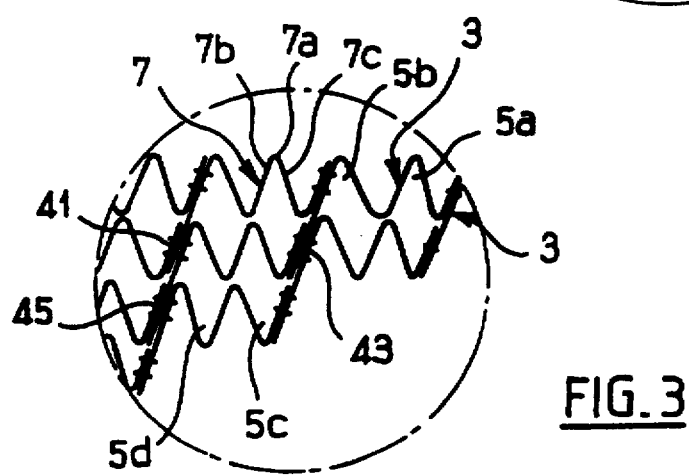
FIG. 3 shows the enlarged detail portion III of FIG. 2.

In FIGS. 1 to 3 (as well as in the other Figures), precedence has been given to a stepped arrangement of the corrugations so that, for example, in the case of a prosthesis having four steps, the zig-zag corrugations of each step define as many rings or annular surface portions 13, 15, 17, 19 as steps 13a, 15a, 17a, 19a, these rings each extending along an axis, 13b, 15b, 17b, 19b, respectively, substantially perpendicular or orthogonal to the longitudinal axis 11. Of course, if these various corrugation steps or rings were not connected to one another, from one step or ring to another, the prosthesis would have no structural cohesion. In order to provide this cohesion at an enhanced level, the solution consists in having at least some (in this case each) of the filaments pass from one step to the next. Thus, each filament or thread forms a sort of "longitudinal stabiliser" 23, 25, 27, 29, 31 by the association of junction portions between steps, such as 33, 35, 37, 39, these portions being secured to one another in steps.

In these figures, by virtue of the zig-zag shape, one of the intermediate segments of these zig-zags extends forward until the beginning of some corrugations of the ring of the following step is formed, and so on. Thus it will be appreciated that, in the embodiments illustrated, each filament making up the prosthesis forms, at each step, only one portion of the corrugated structure of the corresponding ring. In other words, in the embodiments illustrated, each annular portion, e.g., 13, 15, 17, 19 in FIG. 1, is formed from four corrugated portions, each corrugated portion being formed by one of the four filaments making up the entire prosthesis, each filament forming at each step four alternating corrugations before passing to the next step to form another radial annular structure.

In FIGS. 1 to 7, the annular structures in question have been stepped in such a manner that they are arranged adjacent to one another in series along the axis 11. This is in contrast to the embodiments of FIGS. 8 and following, where a distance d of several centimeters separates two consecutive annular corrugated structures along the same axis 11.

In order to produce the prosthesis which has just been described, with reference to FIG. 2 where it is shown unrolled flat, it will be readily appreciated that it is necessary only to close each corrugation step 13a, . . . , 19a on itself along its respective radial axis 13b, . . . , 19b, by fixing the filament ends to one another, for example by a few spot welds.

While in FIG. 2 each filament extends from step to step from one end of the prosthesis to the other, the alternative embodiment of FIG. 3 shows that each filament can be interrupted from place to place along its length. Thus, it is possible, for example, to produce one filament as three successive segments welded end to end, such as at the positions marked 41, 43, and 45 in FIG. 3 where the small transverse bars represent welding areas. Depending on the number of steps, it would even be possible to have a different number of filaments.

Figure 4:
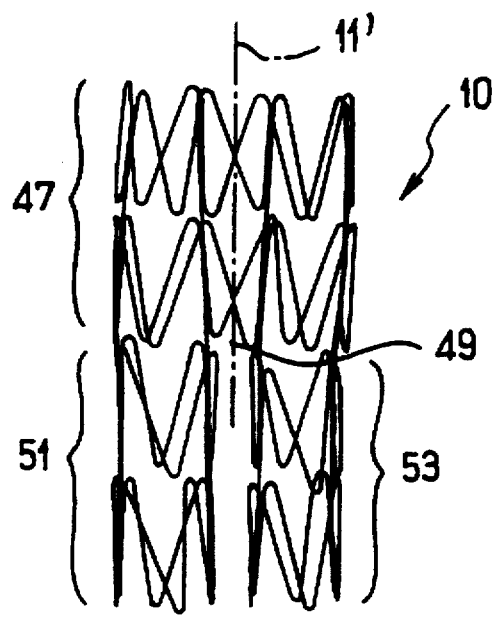
FIGS. 4 and 5 show an embodiment of a forked prosthesis in a perspective view as unrolled flat, respectively.

FIG. 4 shows a forked stent 13 comprising a first branch or main section 47 which extends, for example, up to approximately half or even two thirds of the length of the prosthesis. This main section divides at a branching zone 49 into two secondary tubular branches 51, 53 which are capable of being spaced apart from one another angularly relative to the central axis 11'.

Figure 5:
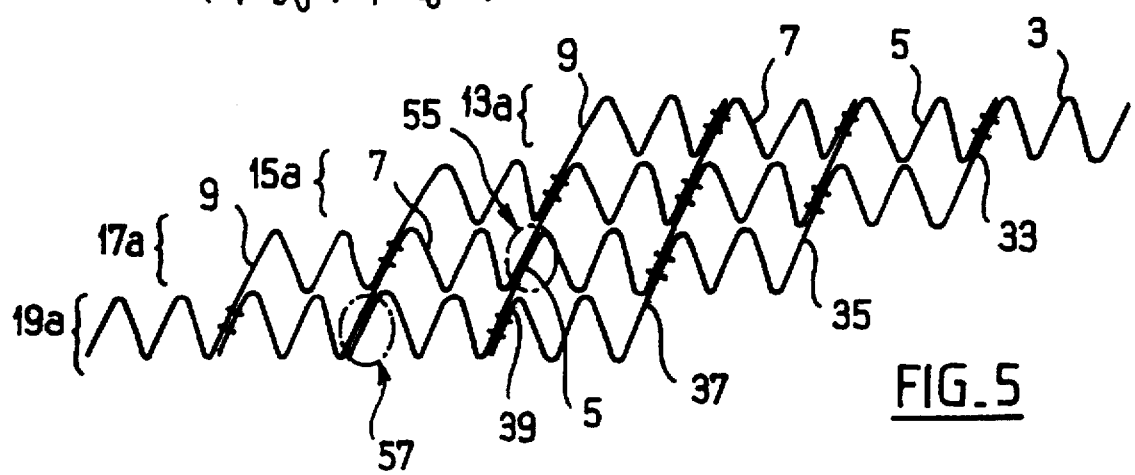

On studying FIG. 5 and comparing it with FIG. 2, it will be appreciated that the two prostheses 1 and 10 (including the alternative embodiment of FIG. 3) can be produced in an exactly identical manner, except at the circled and arrowed places 55, 57 in FIG. 5 where two adjacent filaments of the same step, e.g., filaments 5, 7 and 7, 9 in the case of steps 17a and 19a, respectively, are not connected to one another and therefore remain separate. It will also be appreciated that on branches 51, 53, the number of corrugations per step is less than on the main branch 47.

Figure 6:
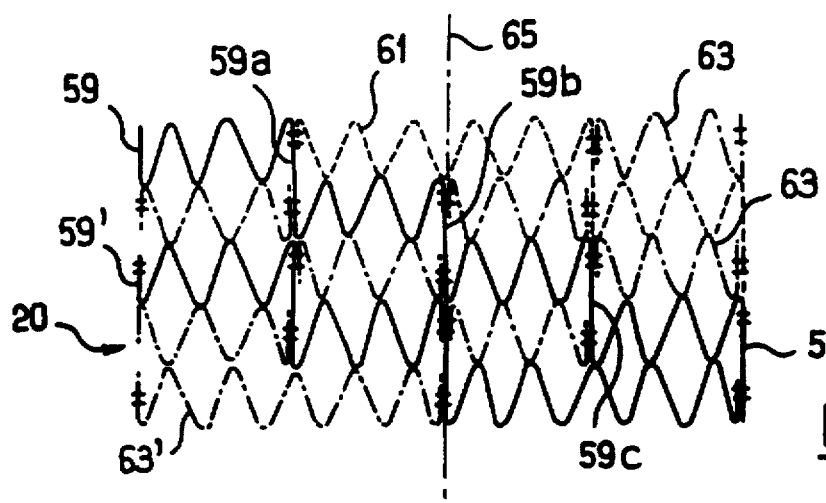

FIG. 6 shows another "simple" stent formed as a single tube. In order to produce it, five types of metal filament 59, 59', 61, 63, 63' have been used, each with at least zig-zag portions, the prosthesis 20 produced thereby again being formed by a sequence of annular structures stepped along the main longitudinal axis 65 of the prosthesis so that the steps together form the desired tubular surface.

Only filaments 63, 63' are not of the "step changing" or "step advancing" type, forming simply by corrugations extending along a single step. In contrast, the filaments 59, 59', 61 change or "jump" steps (in this instance, at 59a, 59b, 59c and 59d in the case of filament 59).

For the sake of clarity and in order to take account of both their similarities and their differences, the various filaments of the prosthesis 20 have been marked with an unbroken line in the case of filaments 59 and 59', with a broken line in the case of filament 61, and with a dot-dash line in the case of filaments 63, 63'.

It will also be noted that what distinguishes the stent 20 from the prostheses 1 and 10 (apart from the method by which it is produced) is that the step changing portions extend parallel to the longitudinal axis 65, not obliquely relative thereto.

The alternative embodiment of FIG. 7 also has step changing filament portions, e.g., 69, 71, and 73, extending parallel to the longitudinal tube axis of the prosthesis 30 shown. Three types of filament—two (75, 77) with step changes and one (79) only with zig-zag corrugations—have been used. The above explanations and the illustration of FIG. 7 are sufficiently clear to produce the prosthesis 30.

FIG. 8 shows the frame or element 40 of a prosthesis for aneurism. The element 40 is formed by two types of fine metal filament 81, 83. In this instance, five identical filaments 83 (or optionally longer or shorter filaments) are used—three for the upper portion and two for the lower portion—in order to define an upper annular corrugated zone and a lower annular corrugated lower zone, both of which are radial relative to the tube axis 11 and which are separated by a distance d.

Rectilinear (i.e., straight) portions forming the longitudinal stabilisers 85, 87, 89, 91 extend between these two zones. The stabilisers extend parallel to the central tube axis 11 and constitute part of the continuous filament 81 which has, alternately at the upper and lower steps of the prosthesis, zig-zag portions 93, 95, and 97 to which the three upper filament portions 83 and the two lower filament portions 83 are secured, e.g., by welding.

In order to secure the structure 40 in its implantation duct, e.g., an artery, the structure is also provided with anchoring hooks 99, 101. These may be formed either from the opposed hooked ends of the filament 831 or from small, separate bars 101 which are hooked at their ends and which are secured, for example by welding, substantially along the axial extent of the longitudinal stabilizers 85, 87, 89, 91 in order to secure the structure axially in one direction and/or in the other direction.

FIG. 9 shows in more detail the welded connection of a small bar 101 both to one of the filaments 83 and to the filament 81.

Figure 10:
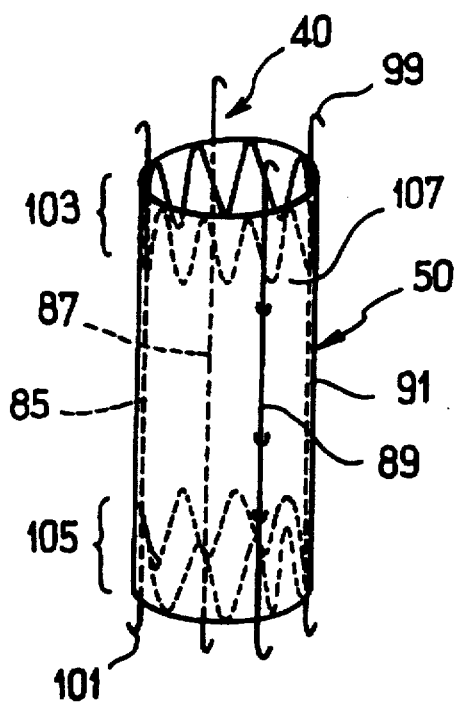

FIG. 10 shows an entire, assembled prosthesis 50 for aneurism of the general type described in FR-A-2 693 366. Frame 40 is as shown in FIG. 8, as are the four axial stabilisers 85, 87, 89, 91, the two upper and lower zig-zag spring structures 103 and 105, and the hooks 99, 101. The covering sleeve 107 for channelling the flow of blood through the prosthesis may be of any sort and attached to the frame as are known in the art.

Figure 11:
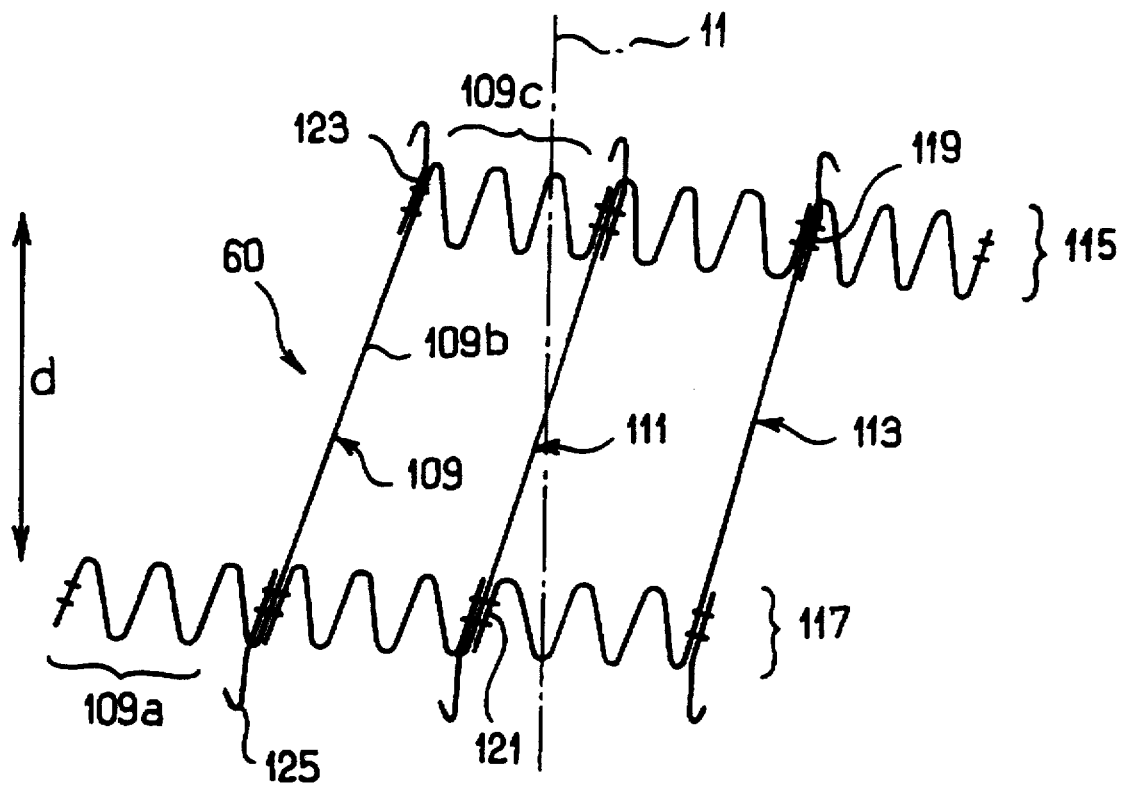
FIG. 11 shows an alternative to the prosthesis frame of FIG. 8.

FIG. 11 shows an alternative embodiment 60 of the frame. This Figure shows three identical filamentary structures 109, 111, 113 arranged side by side and a transverse or skewed relative to the axis 11. Each filamentary structure has a first corrugated or zig-zag portion, e.g., 109a in the case of filament 109, which is extended obliquely over the distance d to the opposite end of the frame by a rectilinear portion, e.g., 109b for the same filament 109. This rectilinear portion is itself extended, at the upper portion, by an additional zig-zag corrugated portion, e.g., 109c, which may be of the same length as the first zig-zag portion. By connecting, e.g., three such structures side-by-side as shown in FIG. 11, e.g., by welding as shown at 119 and 121, it is possible, by winding the structures onto themselves to form a tube, to form two corrugated annular structures 115 and 117 which are connected to one another by the oblique stabilising bars formed by the rectilinear portions, e.g., 109b, of the filaments 109, 111, 113. As in the case of FIG. 8, it is also possible, if necessary, to add welded hooked threads, such as 123, 125.

"Spring-type" filaments could be replaced by memory filaments, e.g., heat memory filaments such as Nithinol® or filaments which can be expanded by ballooning.

We claim:

1. A generally tubular prosthesis for implantation in a human or animal duct to ensure a passageway in said duct, said prosthesis having a tubular surface and a tube axis and being generally axially subdivided into two or more circumferentially oriented hoop-like tubular portions, said prosthesis comprising:

a plurality of discrete structural wires or filaments joined together to form said prosthesis, said wires or filaments each having one or more corrugated portions and at least some of said wires or filaments having one or more generally straightened extension portions;

wherein said hoop-like tubular portions are formed from the corrugated portions of two or more of said wires or filaments, a given corrugated portion forming only an arcuate portion of one of said hoop-like tubular portions; and wherein said extension portions extend between and connect consecutive ones of said hoop-like tubular portions.

2. The prosthesis of claim 1, wherein said plurality of discrete wires or filaments are joined together in side-by-side fashion.

3. The prosthesis of claim 1, wherein at least some of said wires or filaments extend along the entire length of said prosthesis from a first, proximal end to a second, distal end.

4. The prosthesis of claim 1, wherein said corrugations comprise zig-zags having V-shaped apices connected by generally straight intermediate portions.

5. The prosthesis of claim 4, wherein said prosthesis is configured to have a first, as-implanted configuration and a second, radially compacted implantation configuration, wherein said intermediate portions are angularly spaced relative to each other and extend in skewed relation relative to the tube axis when said prosthesis is in said first, as-implanted configuration, and wherein said intermediate portions are disposed generally adjacent to each other and extend generally parallel to the tube axis when said prosthesis is in said second, radially compacted implantation configuration.

6. The prosthesis of claim 1, wherein at least some of said extension portions extending between and connecting consecutive ones of said hoop-like tubular portions are oriented skew relative to the tubular axis.

7. The prosthesis of claim 1, wherein at least some of said extension portions extending between and connecting consecutive ones of said hoop-like tubular portions are oriented generally parallel to the tubular axis.

8. The prosthesis of claim 1, wherein the number of corrugations in two of the corrugated portions forming at least one of said hoop-like tubular portions differs.

9. The prosthesis of claim 1, wherein said tubular portions are arranged generally adjacent to each other.

10. The prosthesis of claim 1, wherein said tubular portions are generally spaced apart from each other.

11. The prosthesis of claim 1, wherein said prosthesis is a forked prosthesis comprising a generally tubular main branch and at least two secondary branches extending from said main branch.

12. A forked prosthesis for implantation in a forked human or animal duct to ensure a passageway in said duct, said forked prosthesis comprising:

a generally tubular main branch and at least two generally tubular secondary branches extending from said main branch, said main branch and said secondary branches having generally tubular surfaces and respective tube axes and being generally axially subdivided into two or more circumferentially oriented hoop-like tubular portions, said main branch and said secondary branches each comprising a plurality of discrete structural wires or filaments joined together to form said main branch and said secondary branches, said wires or filaments each having one or more corrugated portions and at least some of said wires or filaments having one or more generally straightened extension portions;

wherein said hoop-like tubular portions are formed from the corrugated portions of two or more of said wires or filaments, a given corrugated portion forming only an arcuate portion of one of said hoop-like tubular portions; and wherein said extension portions extend between and connect consecutive ones of said hoop-like tubular portions.

13. The prosthesis of claim 12, wherein said plurality of discrete wires or filaments are joined together in side-by-side fashion.

* * * * *